United States Patent
Mansi et al.

(10) Patent No.: US 9,589,379 B2
(45) Date of Patent: Mar. 7, 2017

(54) SYSTEM AND METHOD FOR VISUALIZATION OF CARDIAC CHANGES UNDER VARIOUS PACING CONDITIONS

(71) Applicant: SIEMENS HEALTHCARE GMBH, Erlangen (DE)

(72) Inventors: Tommaso Mansi, Plainsboro, NJ (US); Tiziano Passerini, Plainsboro, NJ (US); Ali Kamen, Skillman, NJ (US); Bogdan Georgescu, Plainsboro, NJ (US); Dorin Comaniciu, Princeton Junction, NJ (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 14/741,540

(22) Filed: Jun. 17, 2015

(65) Prior Publication Data
US 2015/0371437 A1    Dec. 24, 2015

Related U.S. Application Data

(60) Provisional application No. 62/016,220, filed on Jun. 24, 2014.

(51) Int. Cl.
*A61N 1/362* (2006.01)
*G06T 11/60* (2006.01)

(52) U.S. Cl.
CPC ............ *G06T 11/60* (2013.01); *A61N 1/3627* (2013.01); *G06T 2207/10081* (2013.01);
(Continued)

(58) Field of Classification Search
CPC ............ G06T 17/00; G06T 2207/30004; G06T 2207/30048; G06F 19/3437; A61N 1/362;
(Continued)

(56) References Cited

U.S. PATENT DOCUMENTS

| 6,236,878 B1 * | 5/2001 | Taylor et al. ................. 600/416 |
| 7,668,354 B2 | 2/2010 | O'Donnell et al. .......... 382/128 |

(Continued)

FOREIGN PATENT DOCUMENTS

| WO | 2014113746 A1 | 7/2014 |
| WO | 2014133924 A1 | 9/2014 |
| WO | 2015031576 A1 | 3/2015 |

OTHER PUBLICATIONS

Dikici et al., "Quantification of Delayed Enhancement MR Images", In Proc. MICCAI 2004, LNCS 3216, pp. 250-257, 2004.
(Continued)

*Primary Examiner* — Andrew W Johns

(57) ABSTRACT

A system and method for visualization of cardiac changes under various pacing conditions for intervention planning and guidance is disclosed. A patient-specific anatomical heart model is generated based on medical image data of a patient. A patient-specific computational model of heart function is generated based on patient-specific anatomical heart model. A virtual intervention is performed at each of a plurality of positions on the patient-specific anatomical heart model using the patient-specific computational model of heart function to calculate one or more cardiac parameters resulting from the virtual intervention performed at each of the plurality of positions. One or more outcome maps are generated visualizing, at each of the plurality of positions on the patient-specific anatomical heart model, optimal values for the one or more cardiac parameters resulting from the virtual intervention performed at the that position on the patient-specific anatomical heart model.

43 Claims, 9 Drawing Sheets

(52) U.S. Cl.
CPC ............... *G06T 2207/10088* (2013.01); *G06T 2207/10132* (2013.01); *G06T 2207/30048* (2013.01)

(58) Field of Classification Search
CPC .... A61N 1/3627; A61N 1/368; A61N 1/3684; A61B 34/10; A61B 34/104; A61B 34/105
See application file for complete search history.

(56) References Cited

U.S. PATENT DOCUMENTS

| | | | |
|---|---|---|---|
| 7,916,919 B2 | 3/2011 | Zheng et al. | 382/131 |
| 8,098,918 B2 | 1/2012 | Zheng et al. | 382/131 |
| 8,267,927 B2 | 9/2012 | Dalal et al. | 606/34 |
| 8,295,913 B2 | 10/2012 | Haras | 600/427 |
| 8,386,188 B2 | 2/2013 | Taylor et al. | 702/19 |
| 2008/0300588 A1 | 12/2008 | Groth et al. | 606/34 |
| 2009/0124896 A1 | 5/2009 | Haras | 600/427 |
| 2009/0142740 A1 | 6/2009 | Liang et al. | 434/262 |
| 2009/0221999 A1 | 9/2009 | Shahidi | 606/33 |
| 2010/0040272 A1 | 2/2010 | Zheng et al. | 382/131 |
| 2011/0015628 A1 | 1/2011 | Dalal et al. | 606/34 |
| 2011/0251607 A1 | 10/2011 | Kruecker et al. | 606/34 |
| 2012/0022843 A1 | 1/2012 | Ionasec et al. | 703/9 |
| 2012/0041301 A1 | 2/2012 | Redel | 600/425 |
| 2012/0072190 A1 | 3/2012 | Sharma et al. | 703/2 |
| 2012/0121151 A1 | 5/2012 | Bernhardt et al. | 382/131 |
| 2012/0203530 A1 | 8/2012 | Sharma et al. | |
| 2013/0158577 A1 | 6/2013 | Mahon et al. | A61N 7/02 |
| 2013/0197881 A1 | 8/2013 | Mansi et al. | G06F 17/5009 |
| 2013/0197884 A1 | 8/2013 | Mansi et al. | G06F 19/3437 |
| 2013/0216110 A1 | 8/2013 | Zheng et al. | 382/128 |
| 2013/0226542 A1 | 8/2013 | Rapaka et al. | G06F 19/3437 |
| 2014/0022250 A1 | 1/2014 | Mansi et al. | A61B 19/50 |
| 2014/0088943 A1 | 3/2014 | Trayanova et al. | A61B 19/50 |
| 2014/0122048 A1 | 5/2014 | Vadakkumpadan et al. | 703/11 |
| 2014/0136174 A1 | 5/2014 | Audigier et al. | G06F 19/12 |
| 2015/0042646 A1 | 2/2015 | Comaniciu et al. | A61B 19/50 |

OTHER PUBLICATIONS

Peyrat et al., "A Computational Framework for the Statistical Analysis of Cardiac Diffusion Tensors: Application to a Small Database of Canine Hearts", IEEE TMI, 26(11): 1500-1514, 2007.
Mitchell et al., "A Two-Current Model for the Dynamics of Cardiac Membrane", Bulletin of Mathematical Biology, 65(5):767-793, 2003.
Powell, "Developments of NEWUOA for Minimization Without Derivatives", J. Num. Analysis, 2008.
Rapaka, et al., "LBM-EP: Lattice-boltzmann method for fast cardiac electrophysiology simulation from 3d images", In: Medical Image Computing and Computer-Assisted Intervention MICCAI, 2012, pp. 33-40, vol. 7511, Springer Berlin Heidelberg.

\* cited by examiner 400   410   420

SYSTEM AND METHOD FOR VISUALIZATION OF CARDIAC CHANGES UNDER VARIOUS PACING CONDITIONS

This application claims the benefit of U.S. Provisional Application No. 62/016,220, filed Jun. 24, 2014, the disclosure of which is herein incorporated by reference in their entirety.

BACKGROUND OF THE INVENTION

The present invention relates to visualizing the impact of electrical pacing on cardiac function of a patient, and more particularly to automatically calculating heart parameters for various pacing locations and protocols and visualizing the cardiac changes resulting from the various pacing locations and protocols to guide lead placement for interventional therapies.

Heart failure is a major cause of death in the western world. Due to insufficient heart function, heart failure causes dyspnea and fatigue, and can also lead to cardiac arrest. For patients with a prolonged QRS-complex (e.g., QRS≥120 ms) and low left-ventricular ejection fraction, cardiac resynchronization therapy (CRT) is a well-established treatment. CRT consists of implanting electrodes in the heart to pace the muscle artificially and "resynchronize" cardiac contraction. The idea is to pace the myocardium at the right ventricle (RV) endocardium and the left ventricle (LV) epicardium, with given pacing intervals, to resynchronize the cardiac motion and hence re-establish the pumping efficiency of the heart. However, despite strict guidelines, 30% of patients do not respond to CRT. Hence, better patient selection for CRT and improved guidance towards the optimal location of the pacing leads are desirable.

BRIEF SUMMARY OF THE INVENTION

The present invention provides a method and system for visualization of cardiac changes under various pacing conditions for guiding lead placement in interventional therapies. Embodiments of the present invention utilize a patient-specific computational model of cardiac electro-mechanics to calculate heart parameters for various pacing locations and various pacing protocols, and visualize the results on a patient-specific heart mesh that can be overlaid on interventional images for lead placement guidance. Embodiments of the present invention generate outcome maps which visualize cardiac parameters for various pacing locations and protocols as colored meshes.

In one embodiment of the present invention, a patient-specific anatomical heart model is generated based on medical image data of a patient. A patient-specific computational model of heart function is generated based on patient-specific anatomical heart model. A virtual intervention is performed at each of a plurality of positions on the patient-specific anatomical heart model using the patient-specific computational model of heart function to calculate one or more cardiac parameters resulting from the virtual intervention performed at each of the plurality of positions. One or more outcome maps are generated visualizing, at each of the plurality of positions on the patient-specific anatomical heart model, optimal values for the one or more cardiac parameters resulting from the virtual intervention performed at the that position on the patient-specific anatomical heart model.

In another embodiment of the present invention, a patient-specific anatomical model of a target organ is generated based on medical image data of a patient. A patient-specific computational model of organ function is generated based on patient-specific anatomical model of the target organ. A virtual intervention is performed at each of a plurality of positions on the patient-specific anatomical model of the target organ using the patient-specific computational model of organ function to calculate one or more outcome parameters resulting from the virtual intervention performed at each of the plurality of positions. One or more outcome maps are generated visualizing, at each of the plurality of positions on the patient-specific anatomical model of the target organ, optimal values for the one or more outcome parameters resulting from the virtual intervention performed at the that position on the patient-specific anatomical model of the target organ.

These and other advantages of the invention will be apparent to those of ordinary skill in the art by reference to the following detailed description and the accompanying drawings.

DETAILED DESCRIPTION

The present invention relates to visualization of cardiac changes under various pacing conditions for guiding lead placement in interventional therapies. Embodiments of the present invention are described herein to give a visual understanding of the methods for visualization of cardiac changes and guiding interventional therapies. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or available through a network system.

Figure 1:
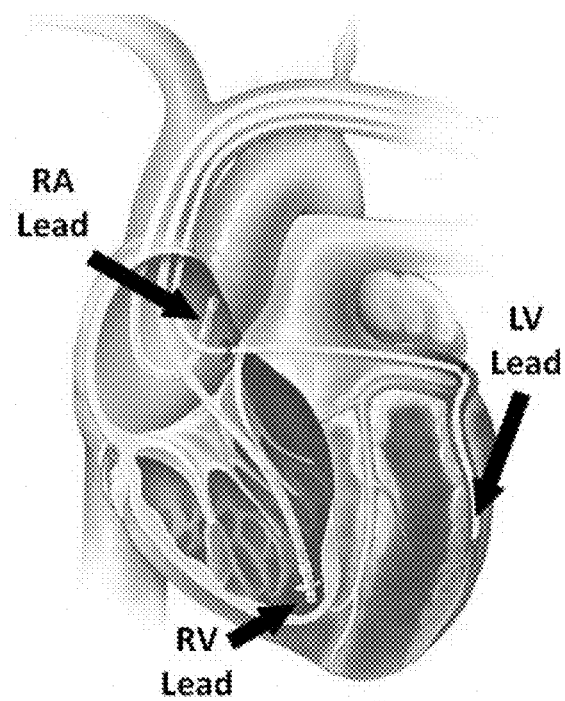
FIG. 1 illustrates an exemplary lead configuration for Cardiac Resynchronization Therapy (CRT)

Cardiac Resynchronization Therapy (CRT) involves placement of an advanced pacemaker to pace the myocardium at the right ventricle (RV) endocardium and the left ventricle (LV) epicardium, with given pacing intervals, to resynchronize the cardiac motion and hence re-establish the pumping efficiency of the heart. CRT is a well-established therapy for heart failure. FIG. 1 illustrates an exemplary lead configuration for CRT including the LV lead, the RV lead, and a left atrium (LA) lead.

Figure 2:
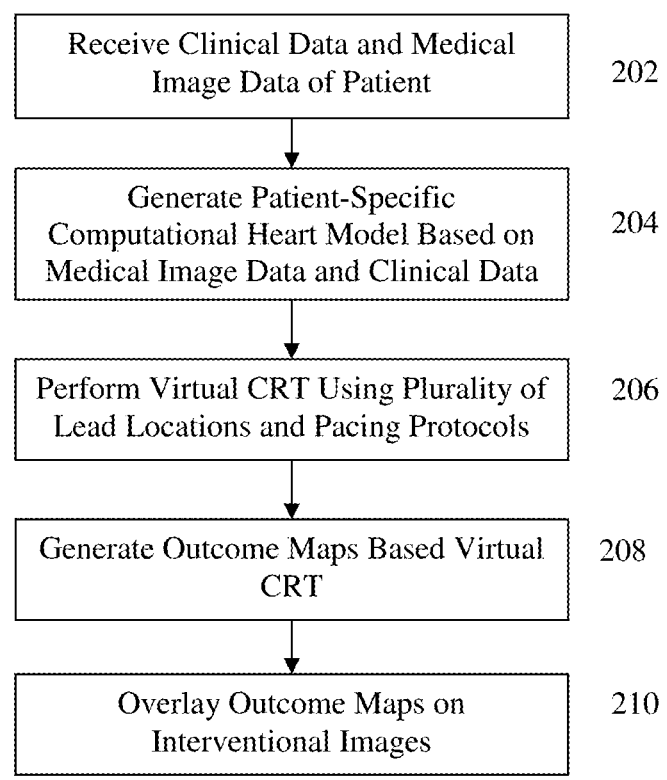
FIG. 2 illustrates a method for guiding a cardiac interventional therapy according to an embodiment of the present invention.

FIG. 2 illustrates a method for guiding a cardiac interventional therapy according to an embodiment of the present invention. The method of FIG. 2 is described herein for guiding CRT, but the present invention is not limited thereto and the method of FIG. 2 may be similarly applied to ablative treatments for cardiac arrhythmias or any other cardiac intervention procedure that is applied at one or more specific locations of the heart. Furthermore, the method of FIG. 2 may be similarly applied to interventional therapies performed at specific locations in other organs (e.g., liver tumor ablation therapy) using computational models for other organs (e.g., liver heat capacity), as well. As illustrated in FIG. 2, at step 202, clinical data and medical image data of a patient are received. The clinical data can include electrophysiology data such as ECG and/or pressure data such as invasive catheter measurements or pressure cuff measurements. The medical image data may be a sequence of 3D medical images acquired over at least one complete heart cycle. In advantageous embodiments of the present invention, the medical images can be MRI images, CT images and/or ultrasound images, but the present invention is not necessarily limited to these imaging modalities. The medical images may be received directly from a medical imaging device, such as an MR, CT or ultrasound scanner, or the medical images may be received by loading stored medical images of a patient.

At step 204, a patient-specific computational heart model is generated based on the medical images and the clinical data of the patient. The patient-specific computational heart model is generated by solving an inverse problem to adjust parameters of the computational heart model such that simulated parameters, such as heart motion, ejection fraction, etc., output by the patient-specific computational heart model match the clinical data and medical images observed for the patient.

Figure 3:
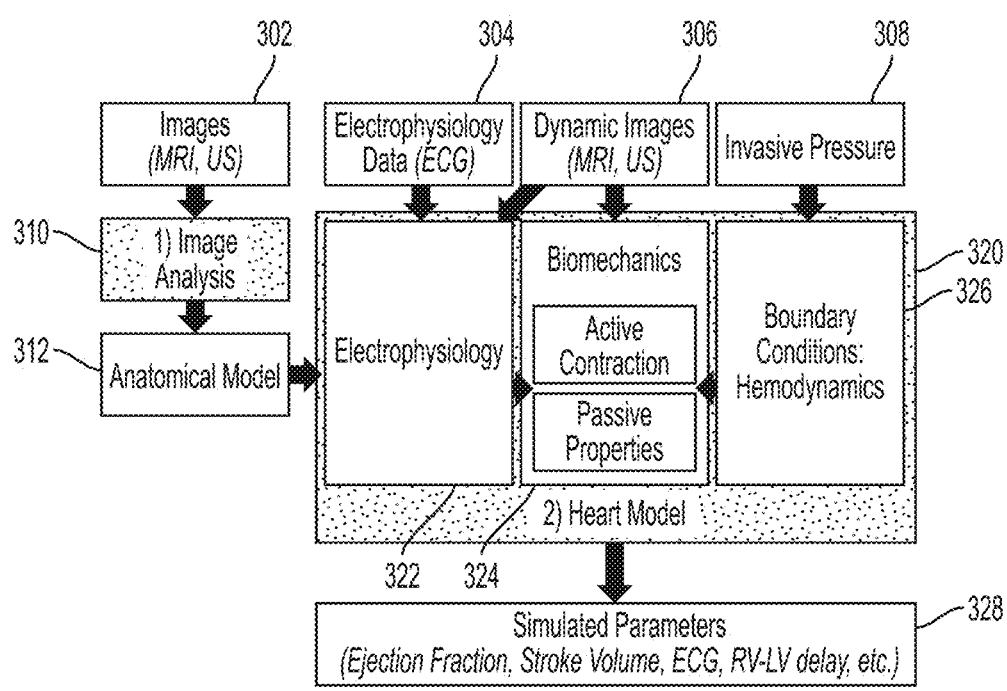
FIG. 3 illustrates a detailed framework of the computational heart model according to an embodiment of the present invention.

FIG. 3 illustrates a detailed framework of the computational heart model according to an embodiment of the present invention. As illustrated in FIG. 3, the patient-specific heart model includes four main models representing cardiac anatomy, cardiac electrophysiology, cardiac biomechanics, and cardiac hemodynamics. These models are connected as follows. Starting from a medical image 302 of the heart (MRI, CT, Ultrasound), at step 310, a detailed patient-specific anatomical model 312 of the patient's heart is generated. In one exemplary embodiment, a detailed anatomical model is generated of the two ventricles only, but the present invention is not limited thereto. Arteries and atria are modeled as boundary conditions of the system. The anatomical model 312 comprises the bi-ventricular geometry, the orientation of myocyte fibers, and any information that varies spatially such as action potential duration, scars, etc. The anatomical model 312 is then given as input to the Heart Model subsystem (step 320), which will compute myocardium motion over time according to three main sub-parts: the cardiac electrophysiology model 322, the cardiac biomechanics model 324, and the cardiac hemodynamics model 326. Each of these models of cardiac function can be fitted to patient data using inverse problem approaches and all available preoperative data such as dynamic images 306, ECG 304, invasive pressure measurements 308, etc. As a result, the simulated parameters 330 match the clinical observations. Once the model is personalized, cardiac therapy, such as CRT, can be simulated by pacing the model at various locations for instance. Clinical parameters are computed from the simulation to quantify the predicted patient response to the therapy. Depending on the application, the model can include of one, several or all of the above-mentioned sub-parts.

In an exemplary embodiment, in order to generate the patient-specific anatomical model 312, anatomical models of the left ventricle (LV) and right ventricle (RV) are extracted from the medical images. Although it is possible to extract models for all of the heart chambers, in an advantageous embodiment, only the geometry of LV and RV are explicitly modeled. If the application targets atrial anatomy, at least one of the atria can be segmented and used as computational domain. For each of the LV and the RV, the heart chamber segmentation can be formulated as a two-step learning problem: anatomical structure localization and boundary delineation. Marginal space learning (MSL) can be used to apply machine learning to 3D object detection. The idea of MSL is not to learn a monolithic classifier directly in the full parameter space of similarity transformations but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. The classifiers in the lower dimensional marginal spaces are used to prune the searching space efficiently. This object localization stage results in an estimated transformation (position, orientation, and scale) of the object (e.g., heart chamber). After automatic object localization, the mean shape model of the object is aligned with the estimated transformation to get a rough estimate of the object shape. The shape is then deformed locally to fit the object boundary using an active shape model (ASM) and a machine learning based boundary detector. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

The patient-specific LV and RV models are then fused into a single anatomical model of the bi-ventricular myocardium. In particular, the LV and RV anatomies are fused into a single volumetric mesh representation, on which vertices are tagged into surface zones according to the underlying anatomy. According to an advantageous implementation, tetrahedral elements can be used to accurately represent the details of the bi-ventricular anatomy. Spatial information can then be mapped onto the anatomical model of the bi-ventricular myocardium. Spatial information, such as scars, border zones, and fibrosis can be identified in images, such as late enhancement MRI. For example, the spatial information may be automatically identified using trained classifiers or may be manually identified by a clinician. The spatial information is mapped onto the tetrahedral mesh representing the bi-ventricular myocardium. This information is important to simulate the electrical wave around scars, in particular for wave-reentry assessment and to correctly capture impaired cardiac mechanics due to ill-functioning or dead cells.

Figure 4:
FIG. 4 illustrates exemplary results of generating a patient-specific anatomical heart model.
Figure 4:
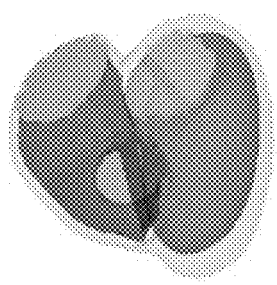
Figure 4:
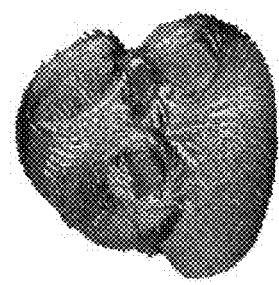

A model of fiber orientation can be automatically calculated based on the patient-specific geometry. In an advantageous implementation, the model of fiber orientation can be automatically calculated using a rule-based approach. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle α, i.e. the angle with respect to the short axis plane, varies linearly across the myocardium, e.g., from −70 on the epicardium to +70 on the endocardium (values that can be defined by the user). Similarly, the sheet direction, which is defined by the angle β with respect to the outward transmural axis, varies transmurally, e.g., from +45 on the epicardium to −45 on the endocardium (values that can be defined by the user). α and β are computed for each point of the volumetric bi-ventricular myocardium mesh between the apex and basal plane based on the geodesic distance to the endocardia and epicardia identified by the facet tags: $\alpha=(d_{epi}\alpha_{endo}+d_{endo}\alpha_{epi})/(d_{endo}+d_{epi})$, where $d_{epi}$, $d_{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. Additional details regarding generating the patient-specific anatomical heart model are described in U.S. Published Patent Application No. 2013/0197881 and U.S. Published Patent Application No. 2015/0042464, which are incorporated herein in their entirety by reference. In another embodiment, the fibers are directly measured in-vivo, in the patient, using MRI diffusion tensor imaging. In another embodiment, an atlas of cardiac fibers could be employed. FIG. 4 illustrates exemplary results of generating a patient-specific anatomical heart model. As illustrated in FIG. 4, image 400 shows segmentation results for segmenting the left and right ventricles in a medical image, image 410 shows the LV and RV fused into a single volumetric mesh, and image 420 shows the model of fiber orientation added to the volumetric mesh.

Once the patient-specific anatomical model 312 is generated from the medical image data of the patient, the patient-specific computational heart model 320 is generated by determining patient-specific parameters for the cardiac electrophysiology model 322, cardiac biomechanics model 324, and cardiac hemodynamics model 326, using the patient-specific anatomical model 312 as input.

The first biophysical phenomenon that needs to be simulated is the cardiac electrophysiology (322), as it commands the cardiac contraction. According to an exemplary embodiment, the cardiac electrophysiology model 322 can compute action potentials over a time period at each of the nodes of the patient-specific anatomical model using a Lattice-Boltzmann method for Electrophysiology (LBM-EP). In an exemplary embodiment, a Mitchell-Schaeffer cellular model can be employed as a tradeoff between model fidelity and complexity, but other cellular models can be employed as well. Patient-specific parameters of the cardiac electrophysiological model, such as an electrical diffusivity and an action potential duration at each of the nodes of the patient-specific anatomical model, can be estimated by solving an inverse problem based on fitting the measured electrophysiology data of the patient. For example, the parameters of the cardiac electrophysiology model can be personalized using ECG measurements, invasive endocardial mappings, or body surface mappings of the patient. Additional details regarding the cardiac electrophysiology model and estimating patient-specific parameters of the cardiac electrophysiology model are described in U.S. Published Patent Application No. 2013/0226542 and U.S. Published Patent Application No. 2015/0042646, which are incorporated herein in their entirety by reference.

The cardiac hemodynamics model 326 can compute cardiac blood flow and pressure over a period of time using a lumped model of intra-ventricular pressure that varies according to models of arterial compliance and atrial contraction. A 3-element Windkessel (WK) model can be used as a model of arterial compliance. The cardiac hemodynamics model can be personalized by estimating patient-specific arterial compliance parameters (e.g., patient-specific parameters of the WK model of arterial compliance) from flow and pressure data of the patient measured from medical images (e.g., Doppler Ultrasound or 2D/4D PC-MRI), cuff pressure measurements, or invasive pressure catheter measurements. Additional details regarding the cardiac hemodynamics model and estimating patient-specific parameters of the cardiac hemodynamics model are described in U.S. Published Patent Application No. 2013/0197881, which is incorporated herein in its entirety by reference.

The cardiac biomechanics model 324 simulates movement of the heart chambers over a time period based on the simulated electrophysiology by the cardiac electrophysiology model 322 and the simulated blood flow and pressure by the cardiac hemodynamics model 326. The cardiac biomechanics model 324 can compute the movement of the heart using the finite element method to solve the dynamics equation $M\ddot{u}+C\dot{u}+Ku=f_a+f_p+f_b$. $\ddot{u}$, $\dot{u}$, and $u$ denote nodal accelerations, velocities, and displacements, respectively. M, K, and C are the mass, stiffness, and Rayleigh damping matrices, respectively. Pressure force $f_p$ is calculated from the cardiac hemodynamics model. The active stress $f_a$ is generated by the myocytes and is computed using a phenomenological model of myocyte contraction, which is mainly governed by the maximum active stress parameter $\sigma_0$. Boundary conditions $f_b$ capture heart attachment at the valve plane through springs and pericardium constraints. The orthotropic Holzapfel-Ogden (HO) constitutive law can be used, among others, defined by the stress-strain energy:

$$\Psi = \frac{a}{2b}e^{b(I_1-3)} + \sum_{i=f,s}\frac{a_i}{2b_i}\left[e^{b_i(I_{4i}-1)^2}-1\right] + \frac{a_{fs}}{2b_{fs}}\left[e^{b_{fs}I_{8fs}^2}-1\right]. \quad (1)$$

Subscripts f and s denote fiber and sheet directions, $I_1$, $I_{4\{f,s\}}$, and $I_{8fs}$ are invariants of the deformation tensor, and $a$, $b$, $a_{\{f,s,fs\}}$, and $b_{\{f,s,fs\}}$ are patient-specific tissue parameters. Equations 1 can be solved according to multiplicative Jacobian energy decomposition (MJED) formulation or the Total Lagrangian Explicit Dynamics (TLED) method for efficient computations. The cardiac biomechanics model 324 can be personalized by estimating patient-specific biomechanical tissue parameters (e.g., stiffness and maximum active stress) based on observed heart movement in the medical images of the patient using inverse problem techniques.

As described herein and illustrated in FIG. 3, the patient-specific computational model of heart function (320) includes a personalized cardiac electrophysiology model 322, a personalized cardiac hemodynamics model 326, and a personalized cardiac biomechanics model 324. It is to be understood that these models are modular and in various embodiments of the present invention, different combinations of these models may be used. For example, the method of FIG. 2 may be implemented using only the electrophysiology model or the electrophysiology model coupled with the biomechanics model, instead of the full computational heart model 320 shown in FIG. 3. The simulated cardiac parameters (e.g., ejection fraction, QRS duration, QT duration, etc.) used to determine the optimal lead placement and pacing protocol may vary based on which components of the computations heart model are used.

As described above, the components (cardiac electrophysiology model 322, cardiac hemodynamics model 326, and the cardiac biomechanics model 324) of the computational heart model 320 are personalized using inverse modeling based on the medical image data and the clinical data of the patient. According to an alternative embodiment, machine learning techniques can be used to directly estimate the personalized model parameters from the medical image data and the clinical data. In addition, the components of the computational heart model can be updated using interventional information (e.g., EP data, pressure measurements, an ablation region, etc.) obtained during the intervention procedure. In this case, outcome maps generated using the computational heart model in steps 206 and 208 can be re-generated using the updated computational heart model for finer guidance.

Returning to FIG. 2, at step 206, virtual CRT is performed using a plurality of lead locations and pacing protocols. Based on the patient-specific computational model of cardiac function, virtual CRT is performed by placing LV and RV leads on the mesh model (i.e., patient-specific anatomical model) and applying electrical stimuli at these locations following a given pacing protocol. The pacing protocol is a set of parameters that controls the pacing at the various leads. In an exemplary implementation, the pacing protocol includes the frequency of each pacing, the interval between LV and RV pacing, and the interval between the first pacing lead and spontaneous depolarization. Pacing protocols can be input following the standard nomenclature of CRT devices (DDD, DDT, etc.) or can be freely set by a user. A library of devices can also be made available with their available protocols as listed in the manufacturer description for ease of use. The electrical stimuli are applied as an additional localized electrical current in the cardiac electrophysiology model. The overall, patient-specific cardiac computational model (e.g., cardiac electrophysiology, cardiac hemodynamics, and cardiac biomechanics) is then recalculated in order to simulate the cardiac function over a plurality of time frames, and parameters of the cardiac function, such as QRS duration, electrical axis, QT duration, ejection fraction, stroke volume, and myocardium strain, are derived from the computational model.

Figure 5:
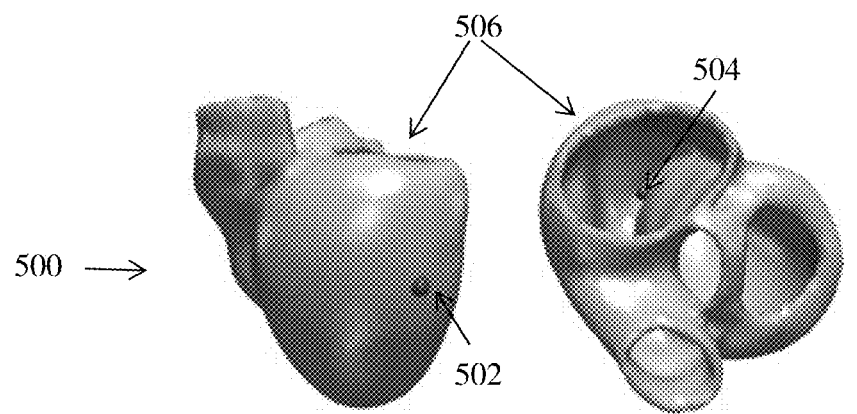
FIG. 5 illustrates an example of interactive virtual CRT.
Figure 5:
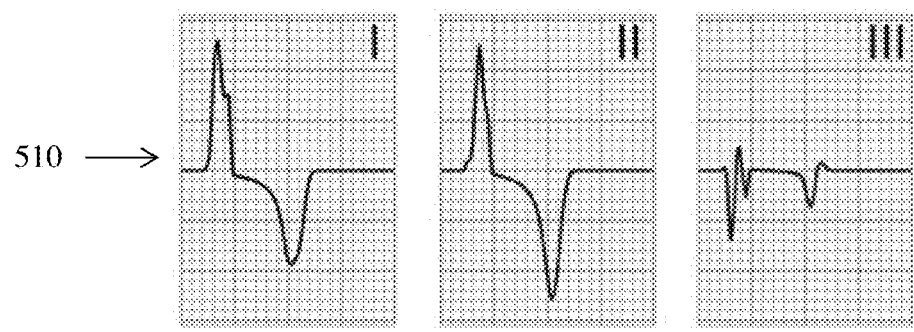

Virtual CRT can be performed interactively. In this case, the user selects on the 3D anatomical heart model the positions of the LV lead and the RV lead and the pacing protocol (e.g., using a user input device, such as a mouse, touch-screen, etc.), and the computational heart model is re-calculated to simulate the cardiac function under the input pacing conditions. Changes in the cardiac electrophysiology, cardiac electrocardiogram (ECG), cardiac motion, and cardiac hemodynamics are computed and displayed to the user. FIG. 5 illustrates an example of interactive virtual CRT. As illustrated in FIG. 5, image 500 shows an LV lead position 502 and an RV lead position 504 input interactively by a user in the patient-specific anatomical heart model 506, and image 510 shows an ECG calculated by the patient-specific computational heart model in the virtual CRT performed using the input LV and RV lead positons 502 and 504.

Although virtual CRT can be performed interactively, in an advantageous embodiment of the present invention, virtual CRT is performed automatically at a plurality of pacing locations for the pacing leads using one or more pacing protocols at each of the pacing locations in order to automatically generate outcome maps that visualize the optimal outcomes for the CRT in order to guide lead placement in the CRT procedure. In an advantageous implementation, the method automatically iterates the virtual CRT simulation over a series of LV and RV position configurations, and for each lead position configuration automatically iterates the virtual CRT simulation over a series of pacing protocols in order to calculate acute cardiac parameters (e.g., QRS duration, QT duration, ejection fraction, stroke volume, etc.) resulting from each of the pacing protocols at each of the lead position configurations. For example, the virtual CRT can be iterated over all points on the LV and RV in the patient-specific anatomical model. In a possible implementation, one of the LV lead position and the RV lead position can be varied while the other one is fixed in order to independently find optimal LV and RV pacing locations. In another possible implementation, both the LV lead position and the RV lead position can be varied, such that virtual CRT is performed for all possible combinations of LV and RV lead positions using each of the pacing protocols. Although this method is described herein as using multiple pacing protocols, it is also possible that a single pacing protocol be used and the lead positions varied for the single pacing protocol.

Returning to FIG. 2, at step 208, outcome maps are generated based on the virtual CRT. The outcome maps visualize optimal outcomes for lead placement based on one or more cardiac parameters resulting from the virtual CRT simulations. The outcome maps can be used for planning the CRT procedure or guiding the clinician towards the optimal lead location in the CRT procedure.

In an exemplary embodiment, LV-only outcome maps and RV-only outcome maps can be generated and used to respectively guide the lead placement for the LV and RV leads. LV-only outcome maps can be generated as follows: Let $X_{RV}$ be a fixed RV lead position. For each possible position of the LV lead, $X_{LV}$, at the LV epicardium and LV endocardium, the cardiac function (e.g., electrophysiology, hemodynamics, and biomechanics) and cardiac parameters $\theta = [\theta_1, \theta_2, \ldots, \theta_n]$ (e.g., $\theta_1$=QRS duration, $\theta_2$=QT duration, $\theta_3$=ejection fraction) are computed using each of pacing protocol $P_j$. Although the cardiac parameters of QRS duration, QT duration, and ejection fraction are used in the above example, the present invention is not limited thereto and other cardiac parameters such electrical axis, stroke volume, myocardium strain, etc. can be used as well. At each position $X_{LV}$ on the 3D mesh (i.e., patient-specific anatomical model), the optimal $\theta_i$ and the associated pacing protocol $P_j$ resulting in the optimal $\theta_i$ are reported for each of the cardiac parameters. The optimal value for each cardiac parameter can be defined based on clinical knowledge. For example, the optimal value for the QRS duration can be the smallest QRS value and the optimal value for the ejection fraction can be the maximum ejection fraction. The optimal value for each cardiac parameter can also be set by a user. In an exemplary embodiment, a respective outcome map is generated for each cardiac parameter $\theta_i$ by assigning a color to each LV point on the 3D mesh to represent the optimal outcome value for the cardiac parameter $\theta_i$ in that point, given a pacing protocol. This results in a respective map that visualizes the optimal LV lead placement to achieve the best possible value for each cardiac parameter. For each cardiac parameter $\theta_i$, a respective outcome map can also be generated to visualize the pacing protocol $P_j$ associated with the optimal cardiac parameter value at each LV position on the 3D mesh. For example, various colors can be assigned to represent various possible pacing protocols, such that a color assigned to each LV point on the 3D mesh represents the pacing protocol that results in the optimal value for the cardiac parameter. Accordingly 2×n outcome maps can be generated to visualize the optimal cardiac parameter value and optimal pacing protocol for each of the n cardiac parameters. Each map can be displayed (e.g., on a display device of a computer system) individually on demand or simultaneously on several views. RV-only outcome maps can be generated similarly to the LV-only outcome maps by fixing the LV lead position $X_{LV}$, varying the RV lead location $X_{RV}$, and computing the cardiac function and cardiac parameters at each RV lead location $X_{RV}$ using each of the pacing protocols.

In another embodiment, bi-lead outcome maps can be generated by varying both the LV lead position and the RV lead position. Bi-lead outcome maps can be generated as follows. For every $X_{LV}$ lead position on the LV epicardium and endocardium, the RV lead position $X_{RV}$ can be varied and for each $X_{RV}$ the parameters $\theta$ are computed for all available pacing protocols P. At each LV point $X_{LV}$, the optimal parameter value (for each of the cardiac parameters) and the associated RV lead location $X_{RV}$ and pacing protocol $P_j$ that result in the optimal parameter value are reported. All maps can be displayed simultaneously. Alternatively, the user can display a map related to one parameter $\theta_i$ in particular and obtain the optimal LV lead position $X_{LV}$ in terms of optimal outcome for that parameter, the associated RV lead position, and the associated pacing protocol. The bi-lead protocol can be extended to a multi-lead procedure in order to guide lead placement with devices with additional leads.

Figure 6:
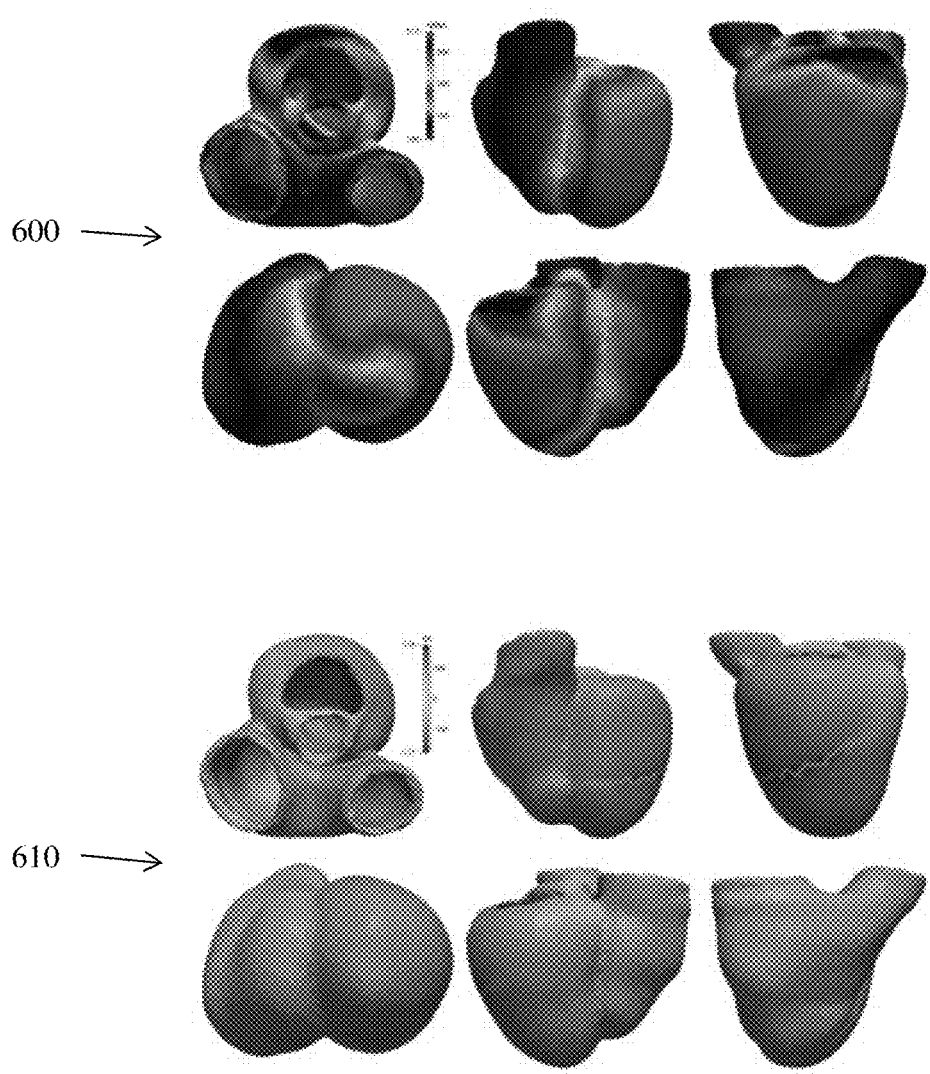
FIG. 6 illustrates an exemplary left ventricle (LV)-only outcome maps for QRS duration and electrical axis cardiac parameters.

FIG. 6 illustrates an exemplary LV-only outcome maps for QRS duration and electrical axis cardiac parameters. The outcome maps in FIG. 6 were generated using a fixed pacing protocol. As illustrated in FIG. 6, image 600 shows an outcome map representing how optimal QRS varies based on LV lead position for a given pacing protocol. Image 610 shows an outcome map representing how optimal electrical axis varies based on LV lead position for a given pacing protocol. Similar maps can be obtained for other cardiac parameters calculated by the patient-specific computational model of heart function.

Figure 7:
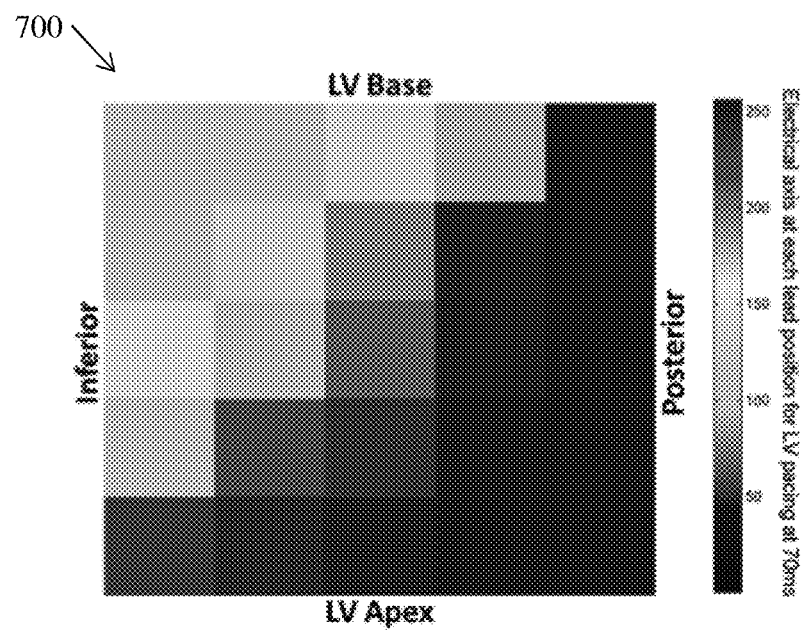
FIG. 7 illustrates an exemplary 2D unfolded outcome map for the LV.

As described above, the outcome maps can be generated using 3D color maps. In another possible embodiment, the outcome maps can be displayed as flat 2D bull's-eye plots. In this case, a polar map is calculated from the 3D mesh for a particular outcome map and used to draw the corresponding bull's-eye plot. In another possible embodiment, different protocols can be tested over a sampled number of points on the LV and the results can be mapped on a square as if the LV were "unfolded". FIG. 7 illustrates an exemplary 2D unfolded outcome map 700 for the LV. The outcome map 700 arranges the sampled points of the LV from an inferior (front) to posterior (back) direction on the horizontal axis and a direction from the LV apex to the LV base on the vertical axis. The color of each point of the outcome map 700 represents the electrical axis value at that lead position for LV pacing at 70 ms. A similar map can be displayed for each pacing protocol and/or each cardiac parameter.

As described above virtual CRT is performed at each possible LV lead location and/or each possible RV lead location on the patient-specific anatomical heart model. In alternative embodiment, only a subset of nodes can be tested and interpolation methods can be used to generate the outcome maps based on the optimal cardiac parameters computed at each of the subset of nodes. Linear, non-linear, or sparse interpolation methods can be employed to perform the interpolation.

Figure 8:
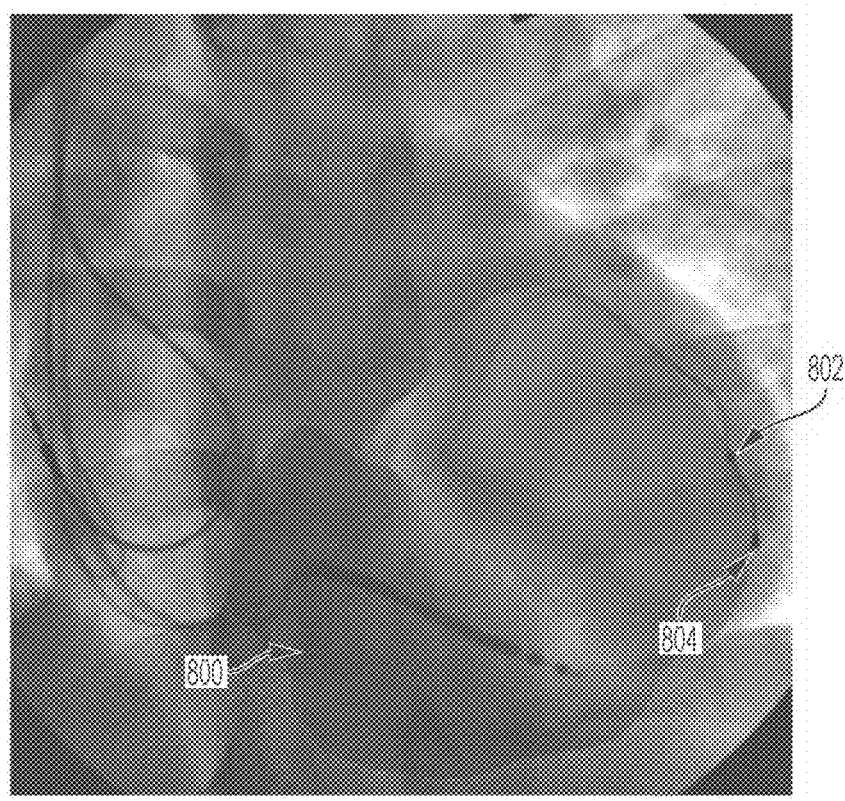
FIG. 8 illustrates an exemplary outcome map overlaid on an interventional image.

Returning to FIG. 2, at step 210, the outcome maps are overlaid on interventional images in an intervention procedure. The 3D outcome maps generated in step 208 can be calculated automatically offline prior to an intervention procedure using pre-operative medical image data or can be calculated online if interventional 3D imaging of the heart (e.g., MRI, ultrasound, DynaCT) is available. The 3D outcome maps can then be registered to interventional images acquired using an interventional imaging system (e.g., angiography system, interventional MRI, EP mapping system, or ultrasound) using standard registration techniques. This registration can be performed in real time or near real time during the intervention procedure. By overlaying one or more 3D outcome maps on the interventional images, the leads and catheters are visualized along the with the outcome map, which enables the user to target the region with optimal outcome as identified by the virtual interventions performed using patient-specific computational model. FIG. 8 illustrates an exemplary outcome map overlaid on an interventional image. As shown in FIG. 8, a QRS outcome map 800 is overlaid on an angiogram showing the CRT leads 802 and 804. A patient-specific model of the coronary arteries can also be overlaid. The model of the coronary arteries can be obtained from pre-operative CT scans or intra-operative images, such as DynaCT.

The method of FIG. 2 can be similarly applied to cardiac ablation therapy. At each position of the 3D heart mesh, a virtual ablation is performed and cardiac parameters are recalculated using the patient-specific computational model of heart function. Virtual ablations using various ablation protocols can be performed at each position. The outcome maps are then generated as described above and can be used to guide cardiac ablation therapy.

Embodiments of the present invention can be similarly applied to other organs (e.g., liver), for example in the case of ablative therapy of abdominal tumors. A patient-specific anatomical model (mesh) of the organ is generated and for each point of the mesh, a virtual ablation is applied and outcome parameters are calculated. A patient-specific computational model of heat diffusion for the organ may be generated and used to perform the virtual ablations. For example, a computational model of liver heat diffusion is described in U.S. Publication No. 2014/0136174 and International Publication No. WO/2014/133924 A1, the disclosures of which are incorporated herein by reference in their entirety. The outcome parameters can include parameters such as recurrence risk, lesion coverage, temperature, etc. The resulting outcome map can then be overlaid on interventional images to guide the ablation procedure.

Although a bi-ventricular anatomical heart model is described above, embodiments of the present invention can also be implemented by modeling the whole heart including all four chambers. For example, this may allow for more precise modeling of CRT.

In a possible embodiment, the method of FIG. 2 can be implemented using a cloud-based system to generate the outcome maps. In this embodiment, computations needed to perform the virtual interventions and calculate the outcome maps can be distributed on a cloud system. In a particular implementation, only the mesh, computational model, and outcome map parameters need to be distributed, thus ensuring privacy and data security.

Figure 9:
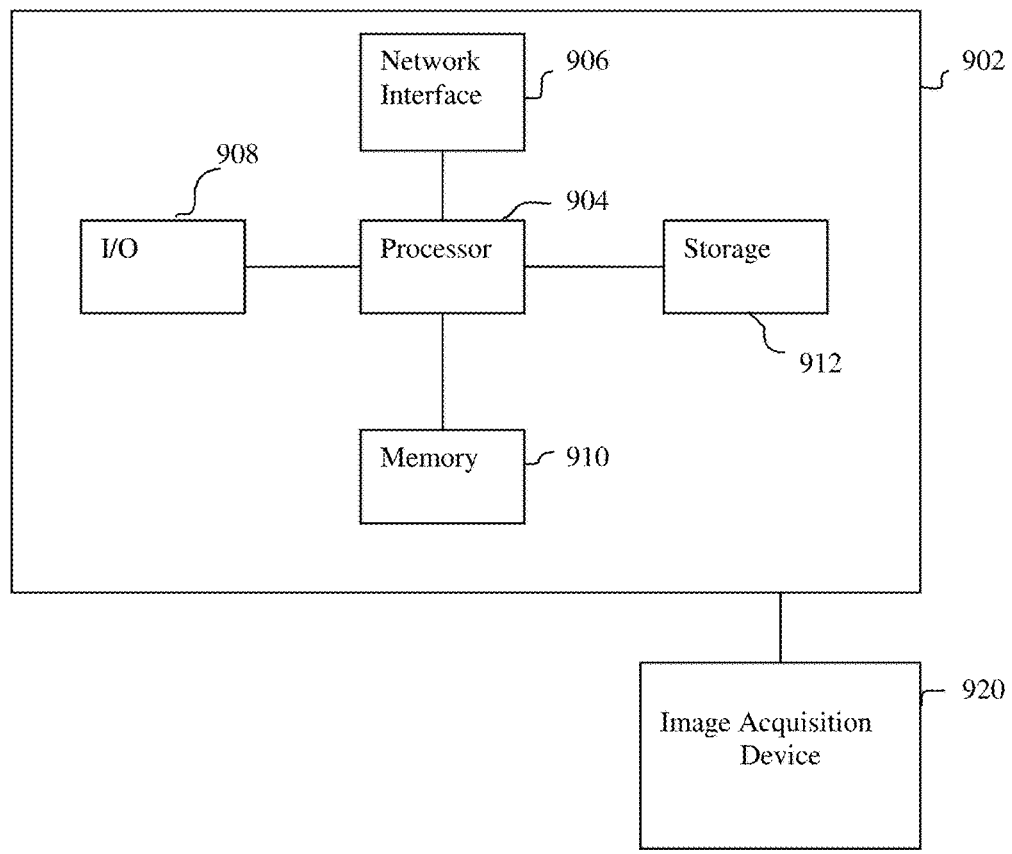
FIG. 9 is a high-level block diagram of a computer capable of implementing the present invention.

The above-described methods for visualizing cardiac changes under various pacing conditions and guiding an intervention procedure can be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 2 and 3 may be defined by the computer program instructions stored in the memory 910 and/or storage 912 and controlled by the processor 904 executing the computer program instructions. An image acquisition device 920, such as a CT scanning device, C-arm image acquisition device, MR scanning device, Ultrasound device, etc., can be connected to the computer 902 to input image data to the computer 902. It is possible to implement the image acquisition device 920 and the computer 902 as one device. It is also possible that the image acquisition device 920 and the computer 902 communicate wirelessly through a network. In a possible embodiment, the computer 902 may be located remotely with respect to the image acquisition device 920 and may perform the method steps as part of a server or cloud based service. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate volumes received from the image acquisition device 920. One skilled in the art will recognize that an implementation of an actual computer could contain other components as well, and that FIG. 9 is a high level representation of some of the components of such a computer for illustrative purposes.

The above-described methods for medical image synthesis may be implemented using computers operating in a client-server relationship. Typically, in such a system, the client computers are located remotely from the server computer and interact via a network. The client-server relationship may be defined and controlled by computer programs running on the respective client and server computers.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for guiding a cardiac intervention, comprising:
   generating a patient-specific anatomical heart model based on medical image data of a patient;
   generating a patient-specific computational model of heart function based on the patient-specific anatomical heart model;
   performing a virtual intervention at each of a plurality of positions on the patient-specific anatomical heart model using the patient-specific computational model of heart function to calculate one or more cardiac parameters resulting from the virtual intervention performed at each of the plurality of positions; and
   generating one or more outcome maps visualizing, at each of the plurality of positions on the patient-specific anatomical heart model, optimal values for the one or more cardiac parameters resulting from the virtual intervention performed at the that position on the patient-specific anatomical heart model.

2. The method of claim 1, further comprising:
   displaying the one or more outcome maps on a display device.

3. The method of claim 1, further comprising:
   overlaying at least one of the one or more outcome maps on an interventional image acquired during an interventional procedure.

4. The method of claim 1, further comprising:
   fusing at least one of the one or more outcome maps with a patient-specific model of coronary arteries.

5. The method of claim 1, wherein performing a virtual intervention at each of a plurality of positions on the patient-specific anatomical heart model using the patient-specific computational model of heart function to calculate one or more cardiac parameters resulting from the virtual intervention performed at each of the plurality of positions comprises:
   performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions.

6. The method of claim 5, wherein performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:
   for each of the plurality of lead positions, performing the virtual pacing using a plurality of pacing protocols.

7. The method of claim 6, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:
   for each of the cardiac parameters, generating a respective outcome map visualizing an optimal value for the cardiac parameter at each of the plurality of lead positions resulting from virtual pacing at each of the plurality of lead positions using the plurality of pacing protocols.

8. The method of claim 7, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model further comprises:

for each of the cardiac parameters, generating a second respective outcome map visualizing, for each of the plurality of lead positions, a pacing protocol resulting in the optimal value for the cardiac parameter at that lead position.

9. The method of claim 5, wherein the virtual pacing is virtual cardiac resynchronization therapy and performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:

performing virtual pacing for a plurality of left ventricle lead positions with a fixed right ventricle lead position using one or more pacing protocols at each of the plurality of left ventricle positons.

10. The method of claim 9, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:

for each of the cardiac parameters, generating a respective left ventricle-only outcome map visualizing an optimal value for the cardiac parameter at each of the plurality of left ventricle lead positions resulting from virtual pacing at each of the plurality of left ventricle lead positions using the one or more pacing protocols.

11. The method of claim 5, wherein the virtual pacing is virtual cardiac resynchronization therapy and performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:

performing virtual pacing for a plurality of right ventricle lead positions with a fixed left ventricle lead position using one or more pacing protocols at each of the plurality of right ventricle positons.

12. The method of claim 11, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:

for each of the cardiac parameters, generating a respective right ventricle-only outcome map showing an optimal value for the cardiac parameter at each of the plurality of right ventricle lead positions resulting from virtual pacing at each of the plurality of right ventricle lead positions using the one or more pacing protocols.

13. The method of claim 5, wherein the virtual pacing is virtual cardiac resynchronization therapy and performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:

for each of a plurality of left ventricle lead positions, performing virtual pacing using one or more pacing protocols at each of a plurality of right ventricle lead positons using the patient-specific computational model of heart function to calculate the one or more cardiac parameters resulting from the virtual pacing performed using the one or more pacing protocols at each of the plurality of right ventricle lead positions.

14. The method of claim 13, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:

for each of the cardiac parameters, generating bi-lead outcome maps visualizing, for each of the plurality of left ventricle lead positions, an optimal value for the cardiac parameter at that left ventricle lead position, a corresponding one of the plurality of right ventricle lead positions resulting in the optimal value for the cardiac parameter at that left ventricle lead position, and a pacing protocol resulting in the optimal value for the cardiac parameter at that left ventricle lead position.

15. The method of claim 1, wherein the one or more cardiac parameters comprise one or more of QRS duration, electrical axis, QT duration, ejection fraction, stroke volume, or myocardium strain.

16. The method of claim 1, wherein performing a virtual intervention at each of a plurality of positions on the patient-specific anatomical heart model using the patient-specific computational model of heart function to calculate one or more cardiac parameters resulting from the virtual intervention performed at each of the plurality of positions comprises:

performing a virtual ablation at each of a plurality of ablation positions on the patient-specific anatomical heart model using the patient-specific computational model of heart function to calculate one or more cardiac parameters resulting from the virtual ablation performed at each of the plurality of positions.

17. The method of claim 1, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:

generating, for each of the one or more cardiac parameters, a respective 3D color map representing the optimal values at the plurality of positions on the patient-specific anatomical heart model for that cardiac parameter.

18. The method of claim 1, wherein the patient-specific computational model of heart function comprises a cardiac electrophysiology model, a cardiac hemodynamics model, and a cardiac biomechanics model.

19. A method for guiding an intervention procedure in a target organ of a patient, comprising:

generating a patient-specific anatomical model of the target organ based on medical image data of the patient;

generating a patient-specific computational model of organ function based on the patient-specific anatomical model of the target organ;

performing a virtual intervention at each of a plurality of positions on the patient-specific anatomical model of the target organ using the patient-specific computational model of organ function to calculate one or more outcome parameters resulting from the virtual intervention performed at each of the plurality of positions; and
generating one or more outcome maps visualizing, at each of the plurality of positions on the patient-specific anatomical model of the target organ, optimal values for the one or more outcome parameters resulting from the virtual intervention performed at the that position on the patient-specific anatomical model of the target organ.

20. An apparatus for guiding a cardiac intervention, comprising:
means for generating a patient-specific anatomical heart model based on medical image data of a patient;
means for generating a patient-specific computational model of heart function based on the patient-specific anatomical heart model;
means for performing a virtual intervention at each of a plurality of positions on the patient-specific anatomical heart model using the patient-specific computational model of heart function to calculate one or more cardiac parameters resulting from the virtual intervention performed at each of the plurality of positions; and
means for generating one or more outcome maps visualizing, at each of the plurality of positions on the patient-specific anatomical heart model, optimal values for the one or more cardiac parameters resulting from the virtual intervention performed at the that position on the patient-specific anatomical heart model.

21. The apparatus of claim 20, further comprising:
means for overlaying at least one of the one or more outcome maps on an interventional image acquired during an interventional procedure.

22. The apparatus of claim 20, wherein the means for performing a virtual intervention at each of a plurality of positions on the patient-specific anatomical heart model using the patient-specific computational model of heart function to calculate one or more cardiac parameters resulting from the virtual intervention performed at each of the plurality of positions comprises:
means for performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions.

23. The apparatus of claim 22, wherein the means for performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:
means for performing the virtual pacing using a plurality of pacing protocols for each of the plurality of lead positions.

24. The apparatus of claim 23, wherein the means for generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:
means for generating, for each of the cardiac parameters, a respective outcome map visualizing an optimal value for the cardiac parameter at each of the plurality of lead positions resulting from virtual pacing at each of the plurality of lead positions using the plurality of pacing protocols.

25. The apparatus of claim 24, wherein the means for generating one or more outcome maps visualizing, at each of the plurality of positions on the patient-specific anatomical heart model, optimal values for the one or more cardiac parameters resulting from the virtual intervention performed at the that position on the patient-specific anatomical heart model further comprises:
means for generating, for each of the cardiac parameters, a second respective outcome map visualizing, for each of the plurality of lead positions, a pacing protocol resulting in the optimal value for the cardiac parameter at that lead position.

26. The apparatus of claim 20, wherein the one or more cardiac parameters comprise one or more of QRS duration, electrical axis, QT duration, ejection fraction, stroke volume, or myocardium strain.

27. The apparatus of claim 20, wherein the means for performing a virtual intervention at each of a plurality of positions on the patient-specific anatomical heart model using the patient-specific computational model of heart function to calculate one or more cardiac parameters resulting from the virtual intervention performed at each of the plurality of positions comprises:
means for performing a virtual ablation at each of a plurality of ablation positions on the patient-specific anatomical heart model using the patient-specific computational model of heart function to calculate one or more cardiac parameters resulting from the virtual ablation performed at each of the plurality of positions.

28. The apparatus of claim 20, wherein the means for generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:
means for generating, for each of the one or more cardiac parameters, a respective 3D color map representing the optimal values at the plurality of positions on the patient-specific anatomical heart model for that cardiac parameter.

29. A non-transitory computer readable medium storing computer program instructions for guiding a cardiac intervention, the computer program instructions when executed by a processor cause the processor to perform operations comprising:
generating a patient-specific anatomical heart model based on medical image data of a patient;
generating a patient-specific computational model of heart function based on the patient-specific anatomical heart model;
performing a virtual intervention at each of a plurality of positions on the patient-specific anatomical heart model using the patient-specific computational model of heart function to calculate one or more cardiac parameters resulting from the virtual intervention performed at each of the plurality of positions; and
generating one or more outcome maps visualizing, at each of the plurality of positions on the patient-specific anatomical heart model, optimal values for the one or more cardiac parameters resulting from the virtual intervention performed at the that position on the patient-specific anatomical heart model.

30. The non-transitory computer readable medium of claim 29, wherein the operations further comprise:
  overlaying at least one of the one or more outcome maps on an interventional image acquired during an interventional procedure.

31. The non-transitory computer readable medium of claim 29, wherein performing a virtual intervention at each of a plurality of positions on the patient-specific anatomical heart model using the patient-specific computational model of heart function to calculate one or more cardiac parameters resulting from the virtual intervention performed at each of the plurality of positions comprises:
  performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions.

32. The non-transitory computer readable medium of claim 31, wherein performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:
  for each of the plurality of lead positions, performing the virtual pacing using a plurality of pacing protocols.

33. The non-transitory computer readable medium of claim 32, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:
  for each of the cardiac parameters, generating a respective outcome map visualizing an optimal value for the cardiac parameter at each of the plurality of lead positions resulting from virtual pacing at each of the plurality of lead positions using the plurality of pacing protocols.

34. The non-transitory computer readable medium of claim 33, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model further comprises:
  for each of the cardiac parameters, generating a second respective outcome map visualizing, for each of the plurality of lead positions, a pacing protocol resulting in the optimal value for the cardiac parameter at that lead position.

35. The non-transitory computer readable medium of claim 31, wherein the virtual pacing is virtual cardiac resynchronization therapy and performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:
  performing virtual pacing for a plurality of left ventricle lead positions with a fixed right ventricle lead position using one or more pacing protocols at each of the plurality of left ventricle positons.

36. The non-transitory computer readable medium of claim 35, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:
  for each of the cardiac parameters, generating a respective left ventricle-only outcome map visualizing an optimal value for the cardiac parameter at each of the plurality of left ventricle lead positions resulting from virtual pacing at each of the plurality of left ventricle lead positions using the one or more pacing protocols.

37. The non-transitory computer readable medium of claim 31, wherein the virtual pacing is virtual cardiac resynchronization therapy and performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:
  performing virtual pacing for a plurality of right ventricle lead positions with a fixed left ventricle lead position using one or more pacing protocols at each of the plurality of right ventricle positons.

38. The non-transitory computer readable medium of claim 37, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:
  for each of the cardiac parameters, generating a respective right ventricle-only outcome map showing an optimal value for the cardiac parameter at each of the plurality of right ventricle lead positions resulting from virtual pacing at each of the plurality of right ventricle lead positions using the one or more pacing protocols.

39. The non-transitory computer readable medium of claim 31, wherein the virtual pacing is virtual cardiac resynchronization therapy and performing virtual pacing for each of a plurality of lead positions on the patient-specific anatomical heart model for one or more electrical pacing leads using the patient-specific computational model of heart function to calculate one or more cardiac parameters resulting from the virtual pacing performed at each of the plurality of lead positions comprises:
  for each of a plurality of left ventricle lead positions, performing virtual pacing using one or more pacing protocols at each of a plurality of right ventricle lead positons using the patient-specific computational model of heart function to calculate the one or more cardiac parameters resulting from the virtual pacing performed using the one or more pacing protocols at each of the plurality of right ventricle lead positions.

40. The non-transitory computer readable medium of claim 39, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:
  for each of the cardiac parameters, generating bi-lead outcome maps visualizing, for each of the plurality of left ventricle lead positions, an optimal value for the cardiac parameter at that left ventricle lead position, a corresponding one of the plurality of right ventricle lead positions resulting in the optimal value for the cardiac parameter at that left ventricle lead position, and a pacing protocol resulting in the optimal value for the cardiac parameter at that left ventricle lead position.

41. The non-transitory computer readable medium of claim 29, wherein the one or more cardiac parameters comprise one or more of QRS duration, electrical axis, QT duration, ejection fraction, stroke volume, or myocardium strain.

42. The non-transitory computer readable medium of claim 29, wherein performing a virtual intervention at each of a plurality of positions on the patient-specific anatomical heart model using the patient-specific computational model of heart function to calculate one or more cardiac parameters resulting from the virtual intervention performed at each of the plurality of positions comprises:

performing a virtual ablation at each of a plurality of ablation positions on the patient-specific anatomical heart model using the patient-specific computational model of heart function to calculate one or more cardiac parameters resulting from the virtual ablation performed at each of the plurality of positions.

43. The non-transitory computer readable medium of claim 29, wherein generating one or more outcome maps visualizing, at each of the plurality of positions on the patient-specific anatomical heart model, optimal values for the one or more cardiac parameters resulting from the virtual intervention performed at the that position on the patient-specific anatomical heart model comprises:

generating, for each of the one or more cardiac parameters, a respective 3D color map representing the optimal values at the plurality of positions on the patient-specific anatomical heart model for that cardiac parameter.

\* \* \* \* \*